US006435002B1

(12) United States Patent
Briggs

(10) Patent No.: US 6,435,002 B1
(45) Date of Patent: Aug. 20, 2002

(54) ASSESSMENT OF THE CONDITION OF FRUIT AND VEGETABLES

(75) Inventor: Peter David Sinclair Briggs, Norwich (GB)

(73) Assignee: Sinclair International Limited, United Kingdom, Norfolk (GB)

( * ) Notice: Subject to any disclaimer, the term of this patent is extended or adjusted under 35 U.S.C. 154(b) by 0 days.

(21) Appl. No.: 09/423,767

(22) PCT Filed: May 15, 1998

(86) PCT No.: PCT/GB98/01300

§ 371 (c)(1),
(2), (4) Date: Feb. 14, 2000

(87) PCT Pub. No.: WO98/52037

PCT Pub. Date: Nov. 19, 1998

(30) Foreign Application Priority Data

May 15, 1997 (GB) .............................................. 9709840

(51) Int. Cl.[7] .......................... B07C 5/02; G01N 21/01; G01N 31/00; G01N 33/02
(52) U.S. Cl. ........................... 73/23.2; 73/23.34; 73/41; 73/865.7; 422/80.08; 422/82.09
(58) Field of Search .............................. 73/23.2, 23.34, 73/41, 37.8, 729.1, 865.7; 422/80, 82.08, 82.09

(56) References Cited

U.S. PATENT DOCUMENTS

| 4,884,696 A | * | 12/1989 | Peleg ........................... 209/545 |
| 5,198,155 A | * | 3/1993 | Etzweiler et al. .......... 261/18.1 |
| 5,269,169 A | * | 12/1993 | Frenkle et al. ............. 73/23.34 |
| 5,313,821 A | * | 5/1994 | Bett et al. ................... 73/23.34 |
| 5,367,899 A | * | 11/1994 | Mookherjee et al. ...... 73/23.34 |
| 5,372,030 A | * | 12/1994 | Prussia et al. .................. 73/37 |
| 5,427,957 A | * | 6/1995 | Itoh ............................. 436/172 |
| 5,621,162 A | * | 4/1997 | Yun et al. ................... 73/23.34 |
| 5,675,070 A | * | 10/1997 | Gelperin .................... 73/23.34 |
| 5,844,124 A | * | 12/1998 | Shimoknawatoko et al. .......................... 73/23.34 |
| 5,844,678 A | * | 12/1998 | Ito et al. ..................... 356/244 |
| 6,006,583 A | * | 12/1999 | Hayashi ..................... 73/23.34 |
| 6,143,245 A | * | 11/2000 | Yan et al. ...................... 422/52 |

* cited by examiner

*Primary Examiner*—Hezron Williams
*Assistant Examiner*—David J. Wiggins
(74) *Attorney, Agent, or Firm*—Townsend and Townsend and Crew LLP

(57) ABSTRACT

An assembly for measuring the condition of fruit and vegetable is disclosed which comprises an expandable resilient bellows arrangement (10) having a passive sensor (22) mounted therein. In use, the bellows (10) can be expanded so as to bring the passive sensor (22) into contact with, or adjacent to, and item of fruit or vegetable whereby the sensor can react to a property of the fruit or vegetable and produces a signal related to that property. The bellows (10) can the be contracted away from the fruit or vegetable. The sensor (22) can detect the properties of, for example, surface gas detection, chlorophyll fluorescence, visible and Near Infra Red spectrometry and change transfer. An arrangement is also disclosed in which a plurality of bellows (10) are mounted on a rotatable mounting (510) whereby by rotation of the mounting (510), the bellows (10) can be brought sequentially into a position in contact with, or adjacent to, a respective fruit or vegetable.

11 Claims, 17 Drawing Sheets

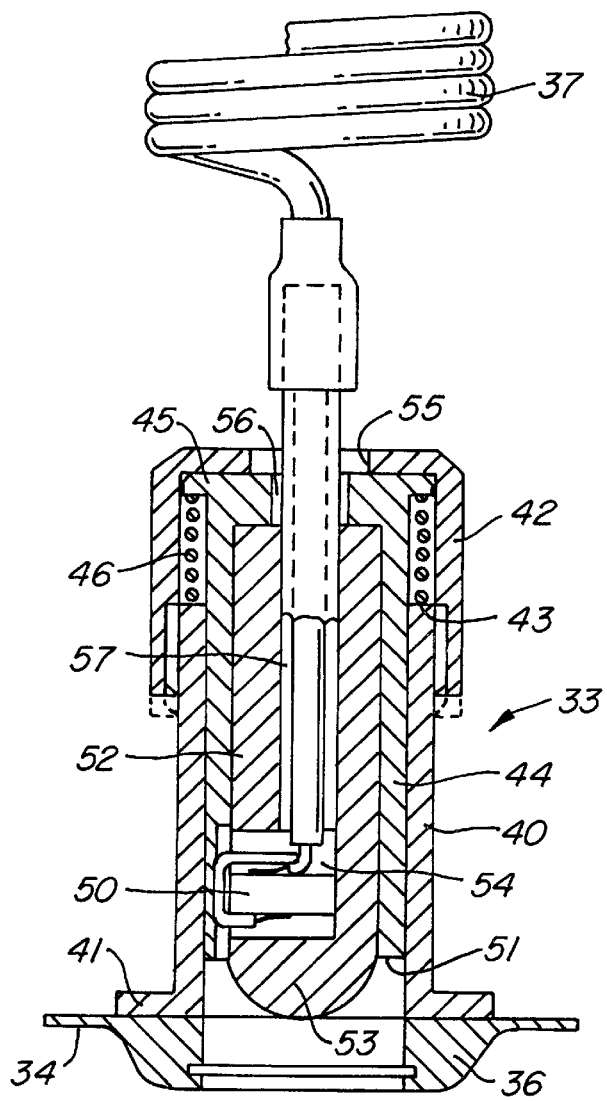
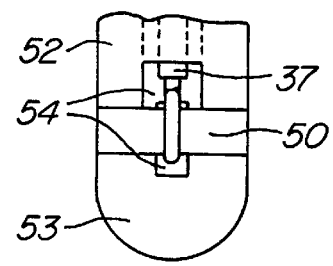
FIG. 18.
FIG. 19.

ASSESSMENT OF THE CONDITION OF FRUIT AND VEGETABLES

BACKGROUND OF THE INVENTION

1. Field of the Invention

This invention relates to the assessment of the condition of fruit and vegetables.

2. Description of the Prior Art

When fruit and vegetables are harvested it is often the case that the crop is of varying degrees of ripeness. Often no special steps are taken to separate the crop according to the extent of ripeness. As a result fruit and vegetables that are sent for storage may already be ripe and ready for consumption and unripe fruit and vegetables may be offered for sale. It is, therefore, a matter of chance to some extent whether the fruit and vegetables at the point of sale are in the optimum condition of ripeness for consumption. Ripe fruit and vegetables put into cold storage tend to be over-ripe by the time they have been removed from the storage and transported to the retail outlet. Frequently such produce cannot even be sold at all and has to be thrown away. This is a serious problem. It has been estimated that a very large quantity of fruit and vegetables is wasted because, being over-ripe when it arrives at the point of sale, it is unsaleable.

Problems of a different kind arise with under-ripe produce. This may look quite acceptable when displayed at the point of sale. However, when a purchaser consumes unripe fruit or vegetables a strongly negative impression is received. This may have the effect of persuading the purchaser not to buy such produce from the same retail outlet again.

EP-A-0 439 405 discloses an apparatus in which a punch is driven towards a fruit at constant speed until it contacts the fruit. The apparatus allows the measurement of the diameter of the fruit and the weight and, if the punch penetrates or crushes the fruit, the ripeness can be measured.

SUMMARY OF THE INVENTION

According to the invention there is provided an assembly for measuring the condition of fruit and vegetables comprising plunger means, and a passive sensor carried by the plunger means, said plunger means being adapted to bring the passive sensor into contact with, or adjacent to, an item of fruit or vegetables whereby the sensor reacts to a property of said fruit item or vegetables to produce a signal related to that property characterized in that the plunger means comprises a resilient bellows assembly which is capable of expansion under the action of pressurized air and retraction by application of a vacuum, the expansion and retraction of the bellows being timed so as to coincide with the presentation of a fruit or vegetable item for assessment.

The invention is particularly suitable for installation in a packhouse where the fruit or vegetables are brought for grading after they have been harvested. Items of fruit travelling on a conveyor can be individually examined using the apparatus of the invention. The results of the examination, that is to say, the signal from the passive sensor, provide an indication of the ripeness or maturity of the fruit item or vegetable and thus the fruit or vegetables can be sorted according to the degree of ripeness or maturity. Under-ripe produce can be held back and sent to storage whereas more mature produce can be forwarded for immediate sale. There can be as many grades between these extremes as may be desired.

The property that the passive sensor is to read can be any property which is indicative of the condition of a fruit or vegetable item. Many of these are well known. The properties that are particularly preferred for measurement by the present invention include surface gas detection, chlorophyll fluorescence, visible and Near Infra Red spectrometry, charge transfer, delayed light emission and resonance.

It is well known that as fruit and vegetables ripen there is emission of gas from their surface. This gas emission is indicative of the condition of the produce. The passive sensor can be adapted to take a sample of this surface gas emission from a fruit or vegetable item, which sample can then be analyzed to provide a signal indicative of the condition of the produce.

It is also known that chlorophyll fluorescence declines as ripening advances. In order to make use of that phenomenon the passive sensor may be an optical device such as one or more optic fibers. Alternatively a passive sensor may be used to scan produce by Near Infra Red spectrometry. This, as is known, gives an indication of the soluble solids in the produce. The major part of the soluble solids in most cases will be sugars so this measurement gives an indication of the ripeness or maturity of the produce. It is also known that Near Infra Red spectrometry can give an indication of material structure and therefore this information can also be used to give an indication of the ripeness or maturity of the produce.

It is further known that different ripeness of produce leads to the produce having different capacitance. Therefore an indication of the ripeness of the product can be provided by the capacitance of the produce. The capacitance of the produce can be measured by having the sensor comprise a charged capacitor, the presence of produce adjacent to which causes a variation in the charge stored in the capacitor, the amount of which is dependent on the capacitance of the produce and hence its ripeness. The change in stored charge on the capacitor can be detected by a second capacitor in what is known as "charge transfer sensing".

BRIEF DESCRIPTION OF THE DRAWINGS

FIG. 18 is a section on an enlarged scale of the impactor of the embodiment of FIG. 17;

FIG. 19 is a fragmentary view of the impactor of FIG. 18; and

DETAILED DESCRIPTION OF SPECIFIC EXEMPLARY EMBODIMENTS

Figure 1:
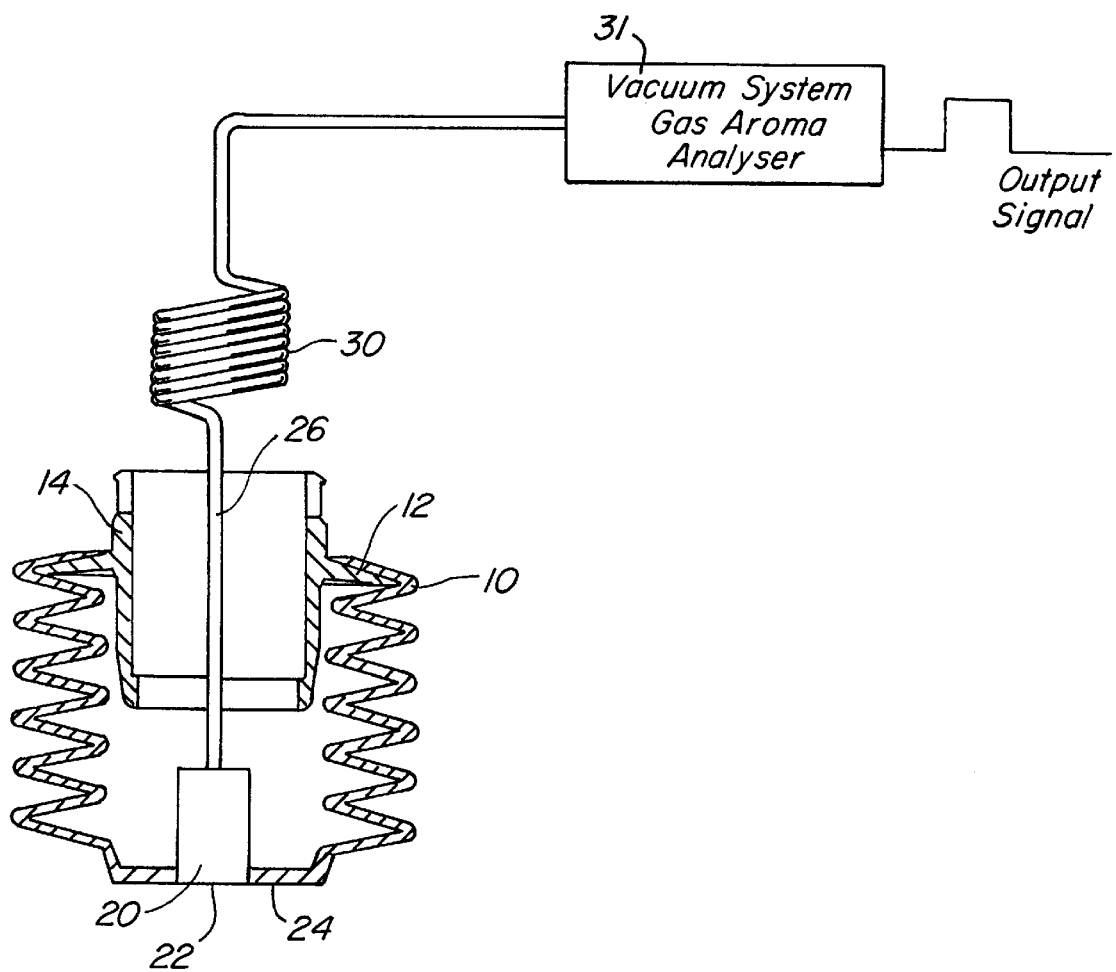
FIG. 1 is a diagrammatic partly sectional elevation of a first embodiment of assembly incorporating a gas sensor.

In the drawings, similar parts of the different embodiments have the same reference numerals. Referring to FIG. 1, the assembly for assessing the condition of fruit or vegetables comprises a bellows 10 of resilient material such as plastics or synthetic rubber and of light construction. The bellows is mounted at one end on an annular flange 12 projecting from a tubular, rigid bellows support 14. The construction of the bellows and means for admitting pressurized air to the bellows to expand the bellows downwardly (as shown in the drawing) and for applying a vacuum to the bellows to retract the bellows upwardly (as shown in the drawing) are described in U.S. Pat. No. 4,217,164 and the contents of this patent are incorporated herein by reference.

A passive gas sensor 20 is mounted at the free or distal end 24 of the bellows and is movable with the expanding and retracting movement of the bellows. As can be seen in the drawing, the gas sensor is located inside the bellows, but has an open mount 22 substantially flush with the free or distal end surface 24 of the bellows. A tube 26 extends from the gas sensor through the bellows support to a gas analyzer measuring means 31. The tube includes a coiled section 30 to enable the gas sensor to move with the bellows.

In use the assembly is positioned above a conveyor carrying fruit or vegetable items. Normally the bellows has a vacuum applied to it to hold it in the retracted position as illustrated in FIG. 1. As an item of fruit or a vegetable passes beneath the bellows the vacuum is replaced by pressurized air causing the bellows to expand and contact the fruit or vegetable item. The gas sensor 20 takes a measured volume of surface gas from the fruit or vegetable item. A vacuum system within the analyzer 31 draws the sample into the analyzer for analysis. Very shortly after contact of the bellows with the fruit or vegetable item a vacuum is again applied to the bellows to retract it. The cycle is then repeated.

The analyzer 31 produces a signal in respect of the gas sample from each item of fruit or each vegetable. This signal can be compared with a predetermined scale in order to obtain an indication of the condition of each said item. That indication can in turn be used to grade the produce, for example, by diverting selected items from the conveyor to be stored until more mature. The passive gas sensor 20 can operate at speeds of approximately 750–1,000 pieces per lane while sensing every piece of fruit or other produce.

Passive gas sensor 20 may be one of various designs known in the art, such as the gas sensor described by M. Benady et al. in their article entitled "Fruit Ripeness Determination by Electronic Sensing of Aromatic Volatiles" published in 1995 *Transactions of the ASAE*, incorporated by reference as though set forth in full herein. That article describes an electronic sniffer having a passive semiconductor gas sensor. An example of a workable gas sensor is a Figaro Gas Sensor TGS822 made by Figaro of Osaka, Japan as the sensor of choice for melons. The sensor detects nine aromatic volatile compounds as described in the published article as well as $CO_2$. The quantity of aromatic volatiles increases with fruit ripening. The particular semiconductor sensor utilized for melons is a tin-dioxide ($SnO_2$) semiconductor, whose conductivity increases in the presence of reducing compounds including combustible gases such as hydrogen, carbon, monoxide, methane and propane, as well as many volatile gases belonging to the alcohol, ketone, ester and benzol groups, some of which occur naturally in ripening fruit.

Figure 2:
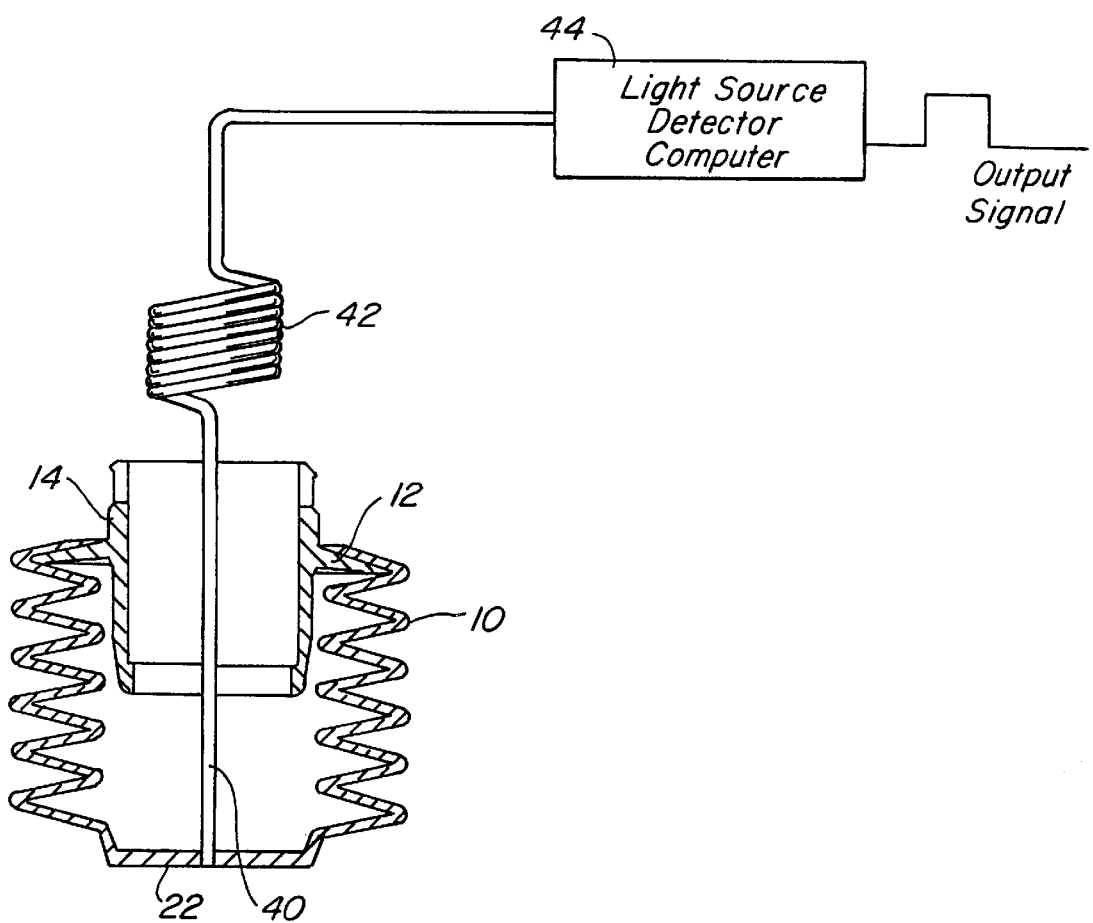
FIG. 2 is a diagrammatic partly sectional elevation of a second embodiment of assembly incorporating an optical sensor.

The embodiment of FIG. 2 is similar to that of FIG. 1 except that a fiber optic bundle 40 replaces the gas sensor 20. The fiber optic bundle is coiled as at 42 to enable it to move with the bellows and is connected to a radiation source and detector assembly 44.

In this embodiment, the radiation source, for example light or Near Infra Red, is directed onto a fruit or vegetable item contacted by or in close proximity to the expanded bellows, and the resulting fluorescence or Near Infra Red spectrum respectively from the item can be detected by the detector assembly 44. The detector provides an output signal which can be compared with a predetermined scale to provide an indication of the condition of the produce.

Figure 3:
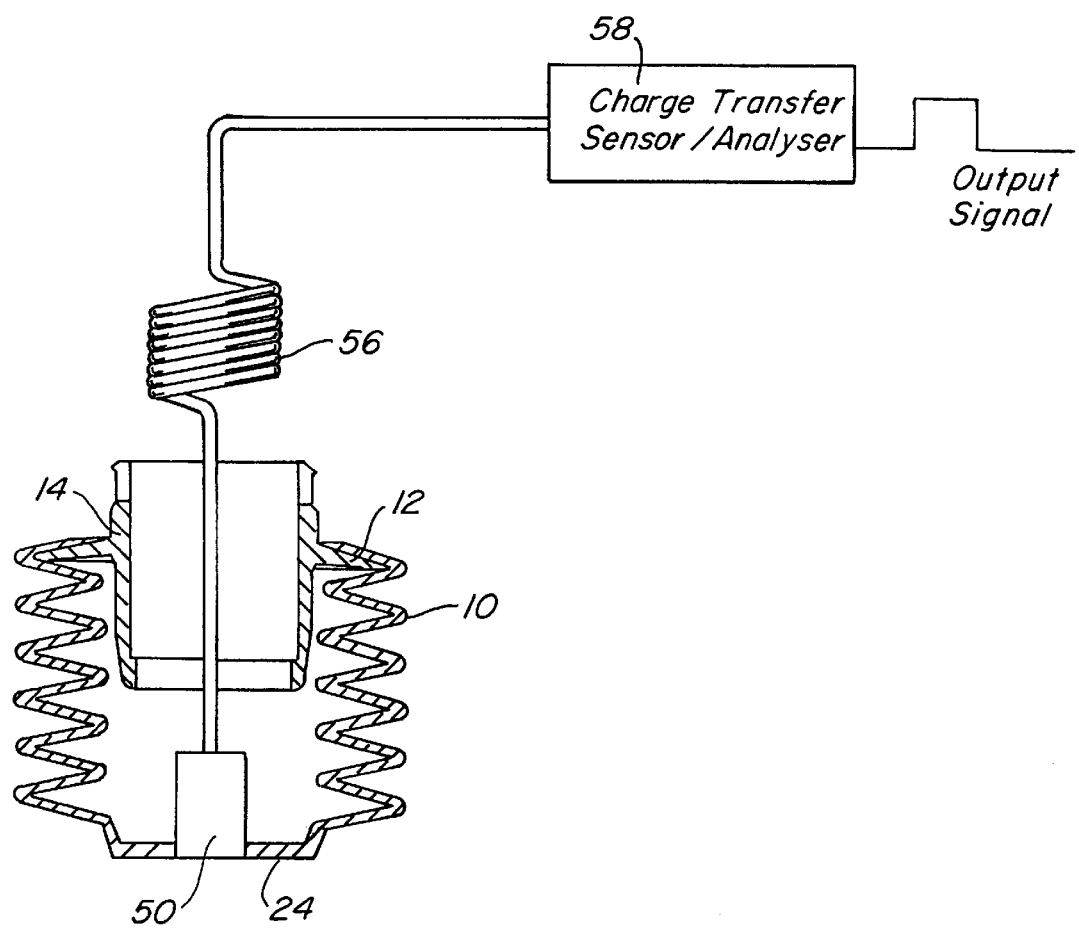
FIG. 3 is a diagrammatic partly section of a third embodiment of assembly incorporating a charge transfer sensor.

The embodiment of FIG. 3 shows an assembly in which the sensor detects the capacitance of a fruit. In this case the sensor 50 comprises a charged capacitor. The passage of produce in close proximity with the sensor 50 induces a change in the stored charge in the sensor 50. The stored charge on the sensor 50 is then discharged into a second detection capacitor where the stored charge is detected in known manner. In practice the sensor and detection capacitors can operate at any required speed to accommodate the feed of produce to the sensor. It is well known that the capacitance of produce depends on the ripeness, and therefore measurement of the capacitance of produce provides an acceptably accurate assessment of ripeness. In the embodiment of FIG. 3, the detection capacitor, switching device and analyzer are all contained within the device indicated at 58 in the figure which is connected to the sensor 50 via a cable 56.

An example of a capacitance system for measuring ripeness is shown in the article by Nelson and Lawrence entitled "Sensing Moisture Content in Dates by RF Impedance Measurements", published in *Transactions of the ASAE*, Vol.

35(2): March–April 1992, wherein a detector in the diode array spectrophotometer contained 1,024 discrete light sensing elements. The diode array detector used by Slaughter et al. and which would be usable in the present invention is a model S1000 manufactured by Ocean Optics of Dunedin, Fla. Fiber optic probe dimeters of between 200 microns and 1,000 microns were utilized. Illumination levels of 100 and 200 watts were evaluated. It was not necessary for the fiber optic tube to actually contact the fruit, resulting in only a small loss of accuracy. A sensor was kept in close proximity to each piece of fruit for 0.25 seconds. The preferred combination of exposure time and probe diameter was 0.25 seconds total exposure when used together with a 200 micron fiber. When the probe was placed 0.5 inches from the surface of the fruit, the correlation only dropped to r=0.89. As used herein, the phrase "close proximity" means 0.5 inches or less.

Another example of an acceptable photodiode is the Hamamatsu Series S6436 photodiodes.

Figure 4:
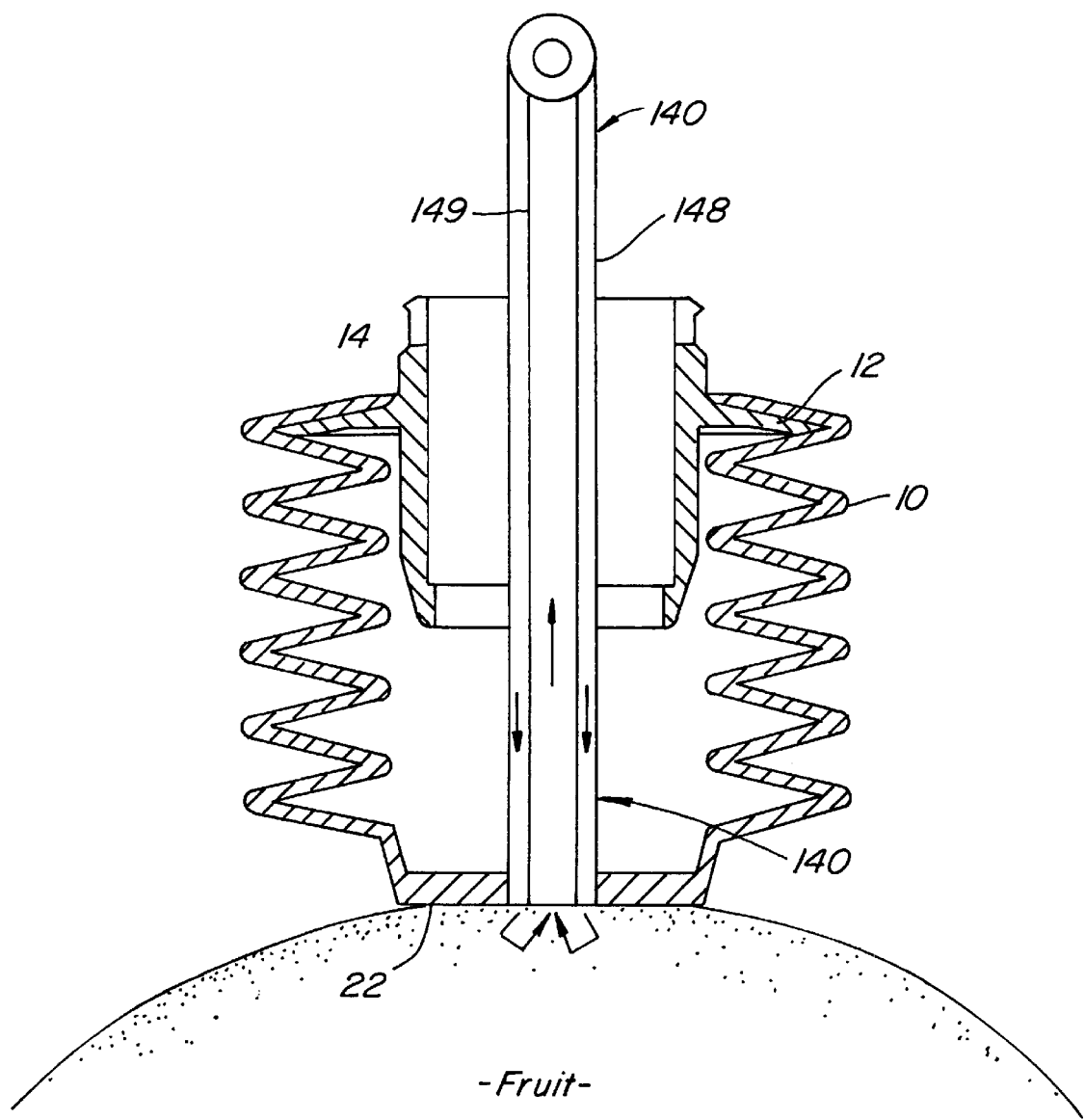
FIG. 4 is a diagrammatic partly sectional elevation of a fourth embodiment of assembly incorporating concentric fiber optic cables contacting a fruit surface.
Figure 5:
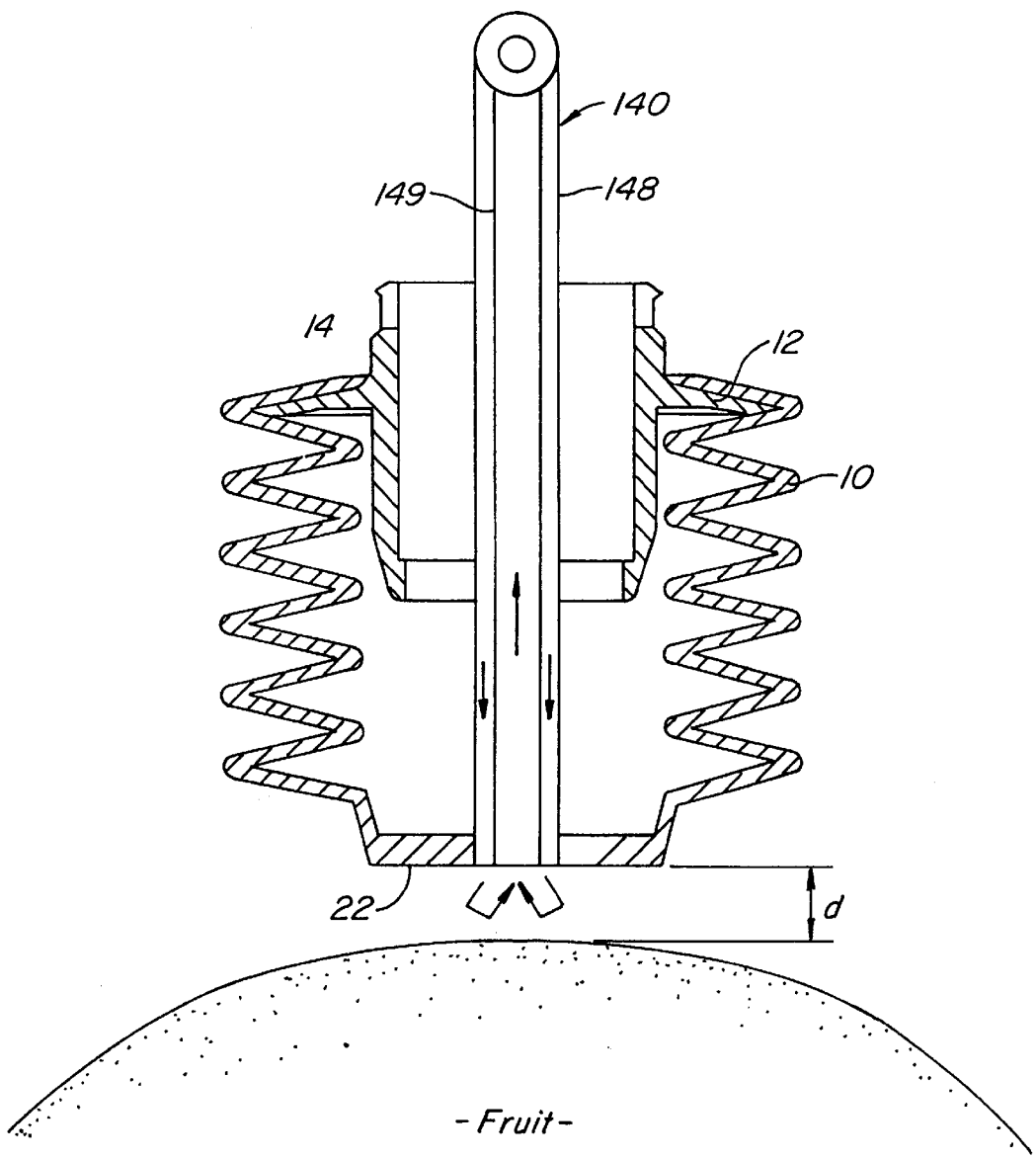
FIG. 5 is a diagrammatic partly sectional elevation of a fifth embodiment of assembly incorporating concentric fiber optic cables brought into close proximity with a fruit surface.
Figure 6:
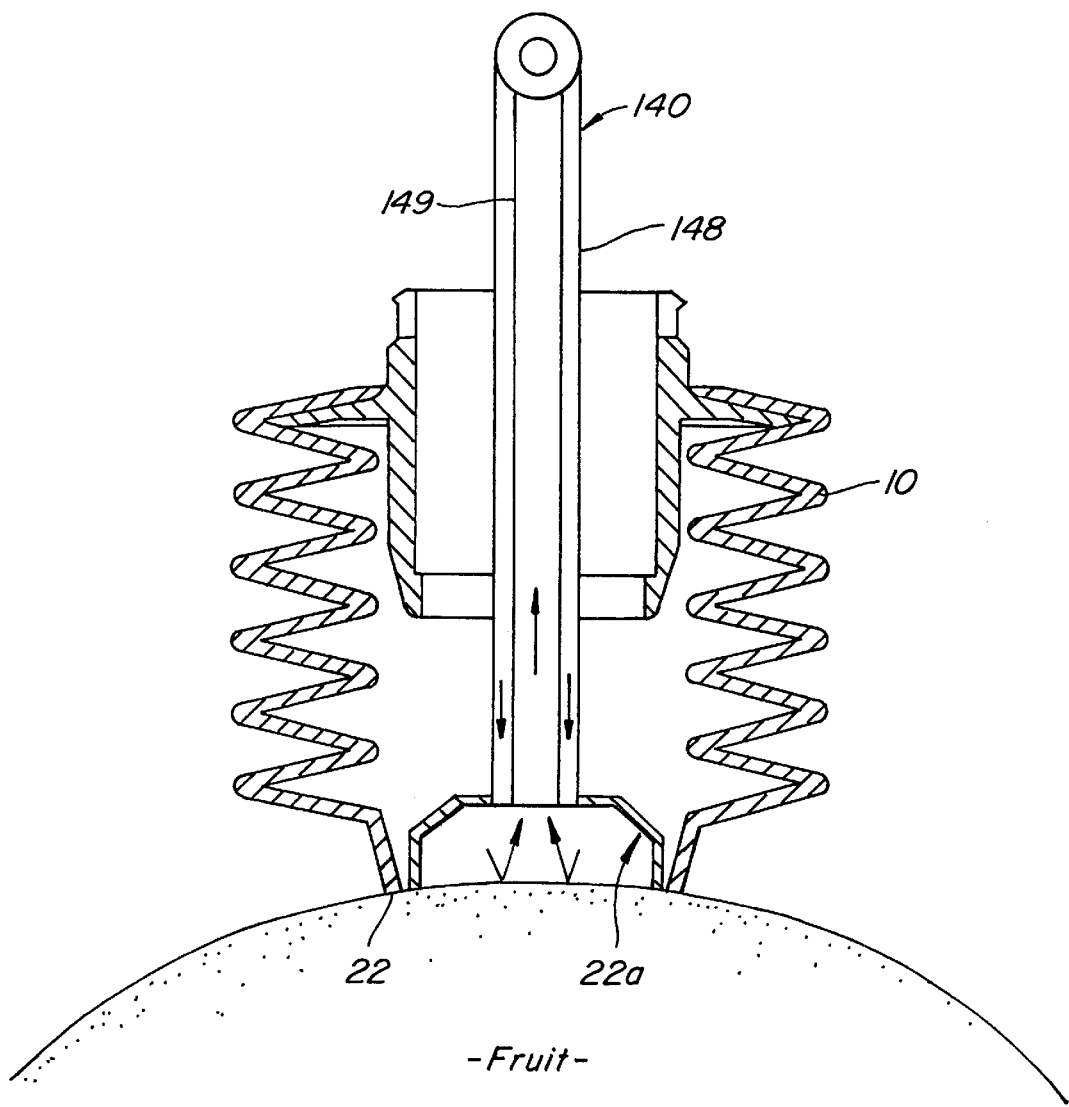
FIG. 6 is a diagrammatic partly sectional elevation of a sixth embodiment of assembly incorporating fiber optic cables held a known standoff distance from the fruit and the device contacting the fruit.

The embodiments of FIGS. 4 and 5 show an assembly in which the sensor comprises a fiber optic bundle 140 including two concentric tubes 148 and 149. Outer tube 148 transmits the incoming light beam and inner tube 149 transmits the reflected beam. In FIG. 4, the distal end 22 of bellows 10 contacts the fruit and the lowermost ends of tubes 148 and 149 also contact the fruit. As shown in FIG. 5, the distal end 22 of bellows 10 may alternatively extend to within close proximity to the fruit surface, which in the case of fiber optics is a distance "d" of 0.5 inch or less. Another option, as shown in FIG. 6, is to form a recess 22a in the distal end 22 of bellows 10 so that the lowermost ends of tubes 148 and 149 are brought to a known standoff distance from the fruit surface when the distal end 22 contacts the fruit.

Figure 7:
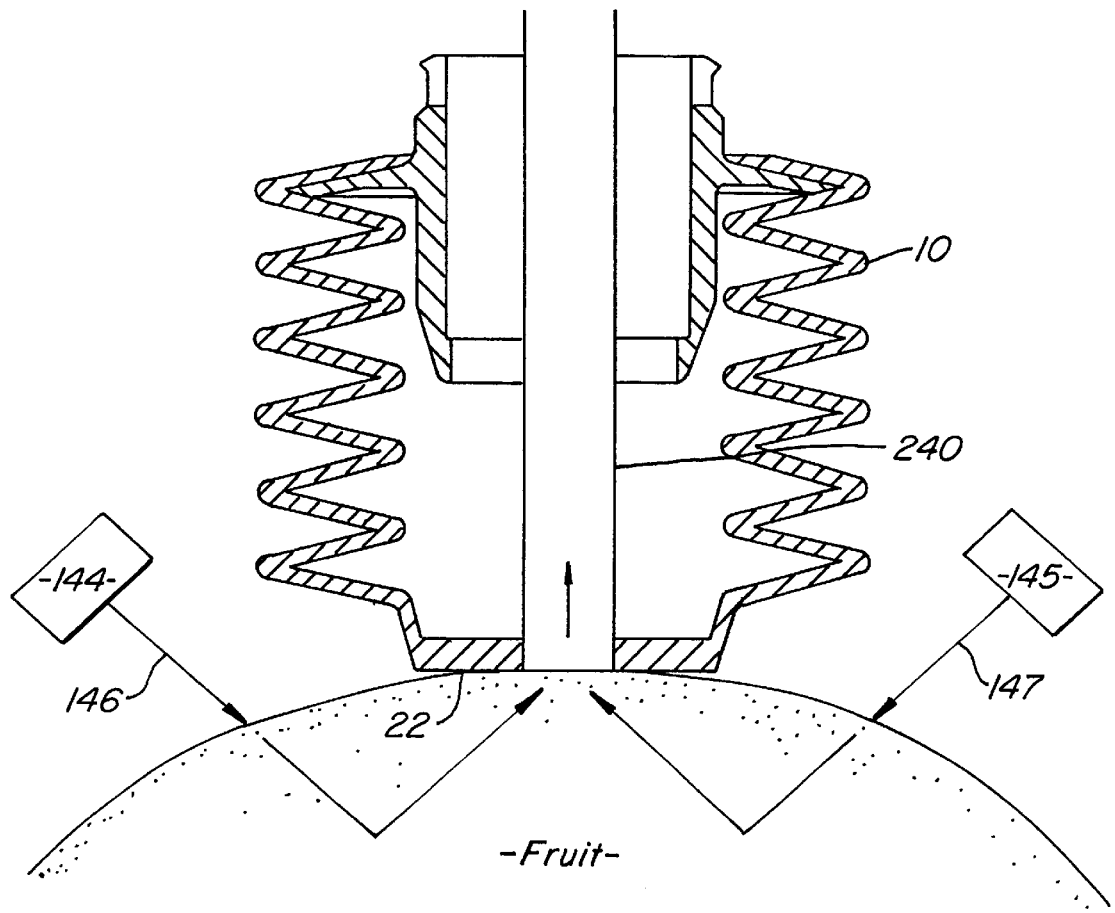
FIG. 7 is a diagrammatic partly sectional elevation of a seventh embodiment of assembly incorporating external light sources which direct light onto the fruit, which light is reflected and collected by a fiber optic cable in the assembly.
Figure 8:
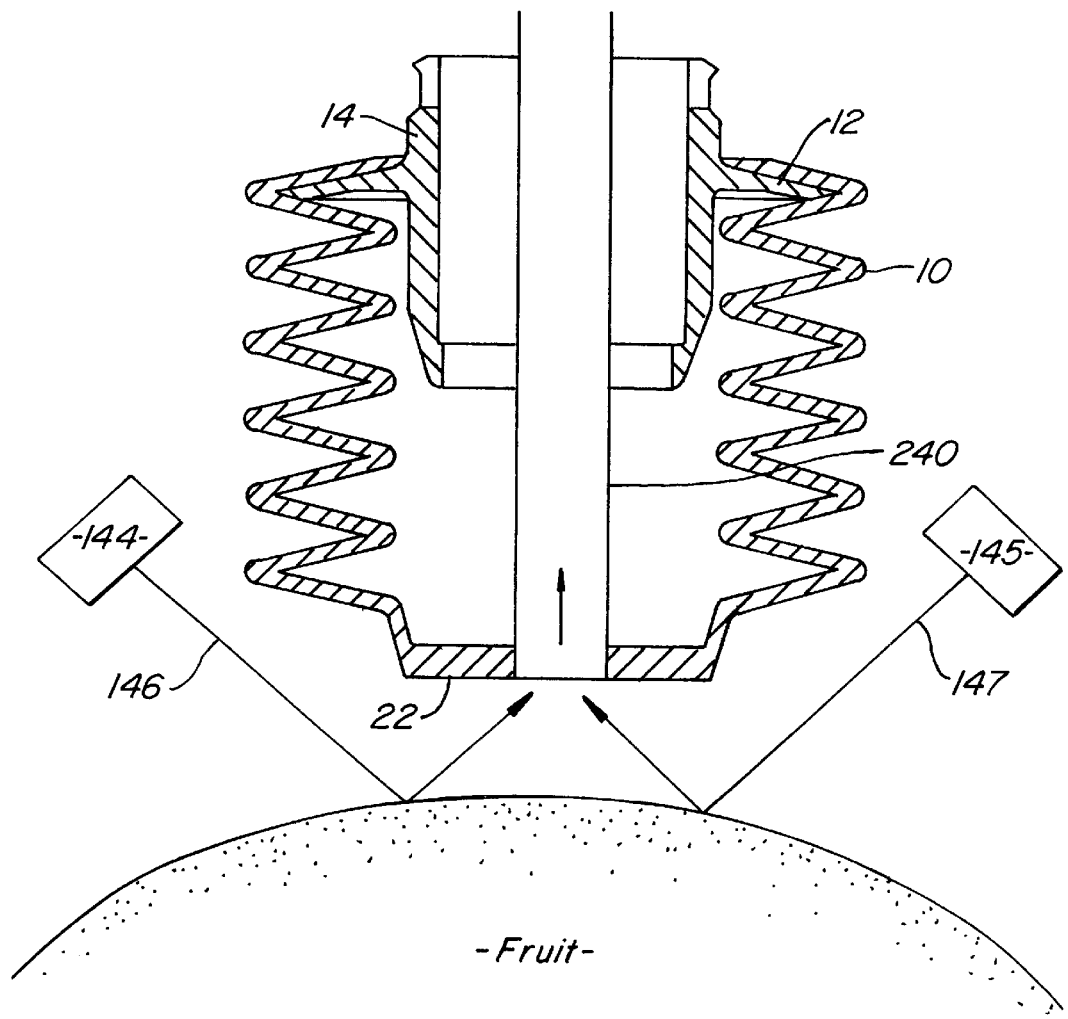
FIG. 8 is a diagrammatic partly sectional elevation of an eighth embodiment of assembly generally similar to that of FIG. 7 but in which there is no contact between the fruit and the assembly.

FIGS. 7 and 8 show further embodiments of assembly in which the sensor comprises a fiber optic tube in which radiation sources 144 and 145 are positioned outside bellows 10 and the output beams 146 and 147 penetrate the fruit, causing a fluorescent beam to enter the tube 240. In the embodiment of FIG. 7, the distal end 22 of the bellows is brought into contact with the fruit surface whereas in the embodiment shown in FIG. 8, the distal end 22 of bellows 10 is brought into close proximity with, but does not contact, the fruit surface. Output beams 146 and 147 are reflected off the fruit into tube 240.

Figure 9:
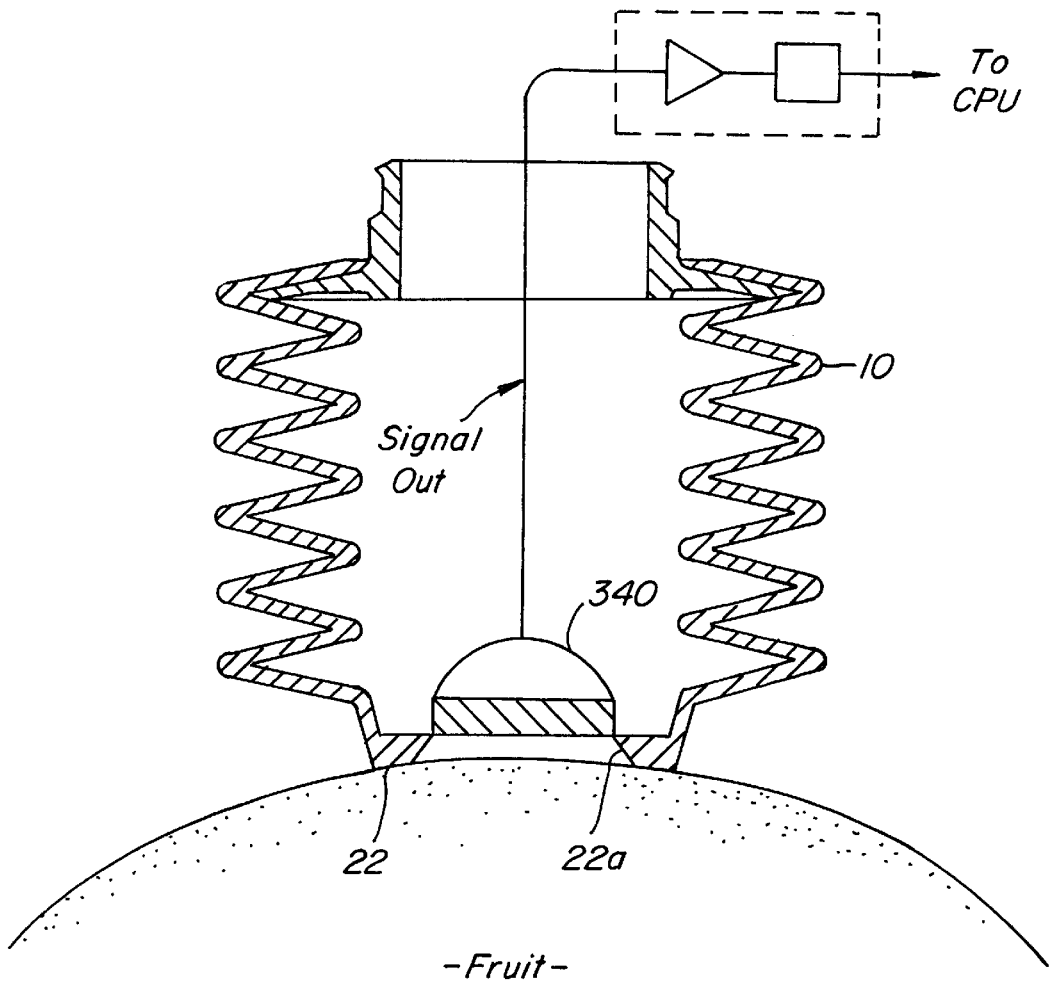
FIG. 9 is a diagrammatic partly sectional elevation of a ninth embodiment of assembly in which a photodetector is carried in the assembly.

FIG. 9 shows a still further embodiment of assembly in which the sensor comprises a photodetector 240 carried in a recess 22a in the distal end 22 of bellows 10, which either senses reflected light from light sources positioned outside bellows 10 or senses light reflected from a light source carried by photodetector 240.

An example of an optical system known in the prior art is one described in the article entitled "Non-Destructive Sensing of Quality Attributes in Peaches and Nectarines", 1997, by David Slaughter et al., of the University of California, Davis. That article is incorporated herein by reference. The system described therein is a high speed spectrophotometric system for measuring near infrared properties of intact peaches and nectarines. The system included three major components: 1) a high speed diode array spectrophotometer, 2) a near infrared illumination source and 3) a high speed computer system. The light technique could be used in conjunction with the present invention as described in greater detail in the Beaudray et al. article.

While in the embodiment of FIG. 9 a photodetector 340 is described as being present in the distal end 22 of the bellows 10, it is to be understood that any number of sensors can be provided in the recess 22a and these sensors may be of the same type or of different types. In these circumstances the sensors will be of a sufficiently small size and preferably will be miniature sensors.

A related optical technique is chlorophyll fluorescence, as described by Randolph M. Beaudry et al. in the article "Chlorophyll Fluorescence: A Nondestructive Tool for Quality Measurements of Stored Apple Fruit", 1997, which article is incorporated herein by reference. The article describes optically sensing the chlorophyll fluorescence of various apples. The apples were placed 4 mm from the end of a fiber optic light guide of a pulse-modulated fluorometer. The particular fluorometer was a Model OS-500 made by Opti-Science, U.S.A. (See the Chlorophyll Fluorescence, pages 591–596.) This article is incorporated herein by reference. The article discloses the use of parallel plate capacitors to measure moisture contents of the flesh and pits of dates and the results were encouraging.

Figure 10:
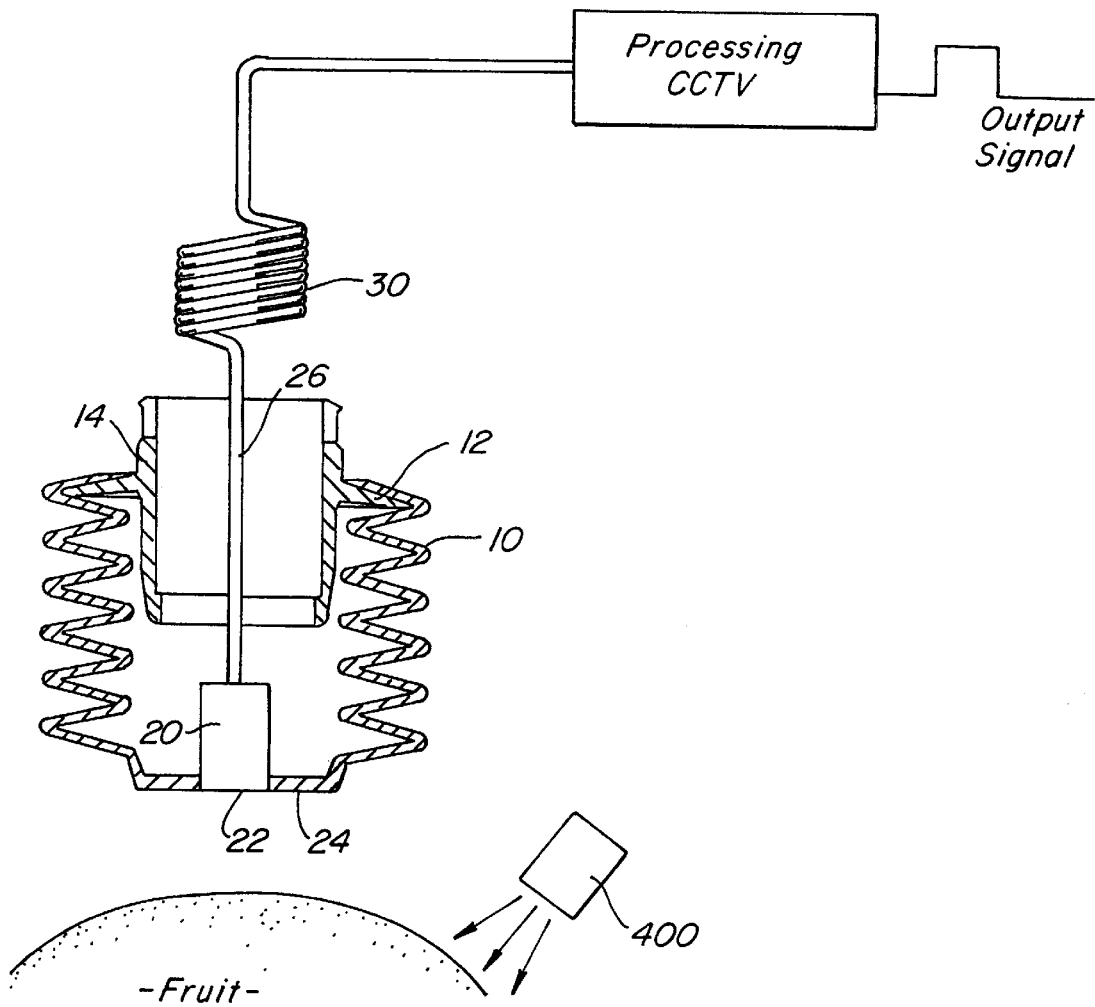
FIG. 10 is a diagrammatic sectional elevation of a tenth embodiment of assembly in which maturity is detected using delayed light emission.

Referring now to FIG. 10, there is shown an embodiment of assembly in which the sensor detects the intensity of delayed light emission (DLE) from a fruit after it has been illuminated by an external light source 400. After illumination by the light source 400, the fruit will emit a low intensity light whose intensity will depend on the maturity of the fruit. The use of delayed light emission to measure the maturity of tomatoes is explained in more detail in an article entitled "Measurement of Tomato Maturity by Delayed Light Emission" by W. R. Forbes et al. in The Journal of Food Science—Volume 50 (1985).

Figure 11:
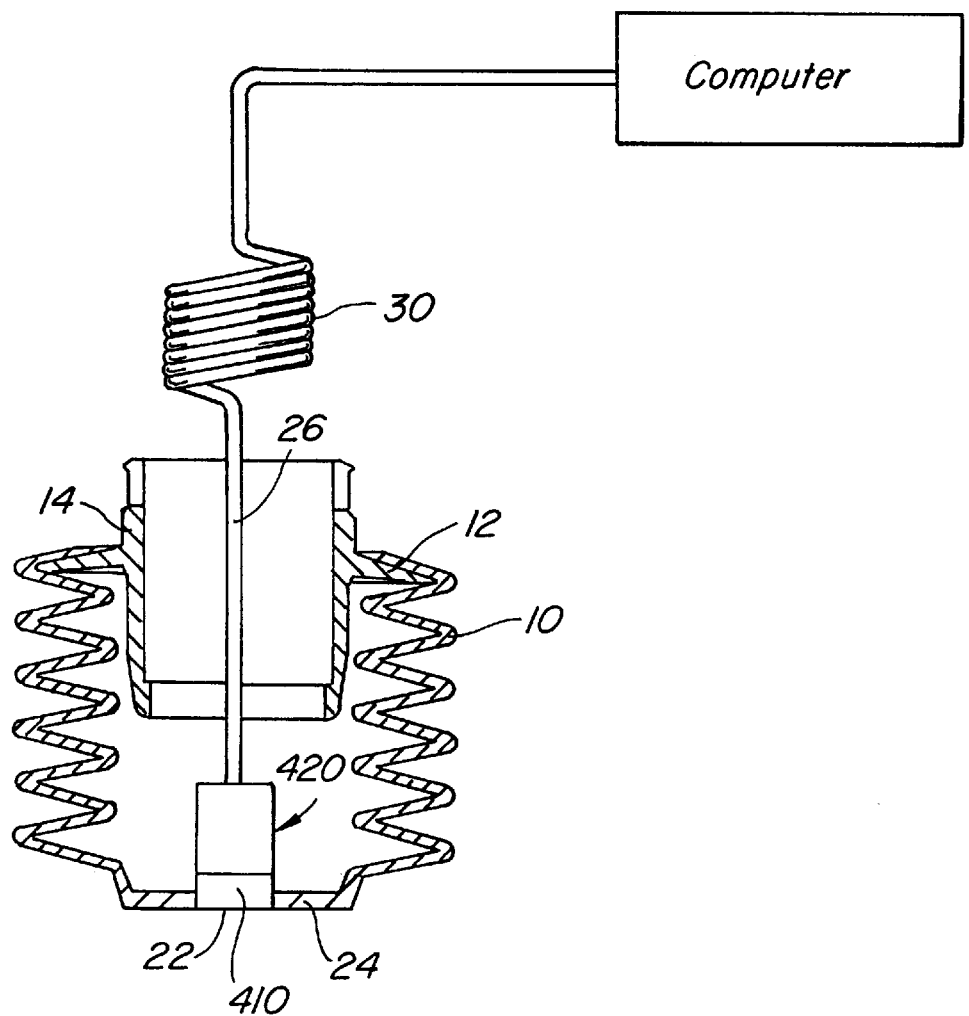
FIG. 11 is a diagrammatic sectional elevation of an eleventh embodiment of assembly in which maturity is detected using resonance.

A still further embodiment of an assembly is shown in FIG. 11 in which the sensor comprises a piezoelectric microphone 410. In this embodiment, the bellows 10 incorporates a plunger 420 which when the bellows 10 expands taps the surface of the fruit. After a series of gentle taps, the fruit resonates at a frequency determined by its weight and maturity. The detected frequencies are processed by a computer which produces an output indicative of the maturity of the fruit.

Figure 12:
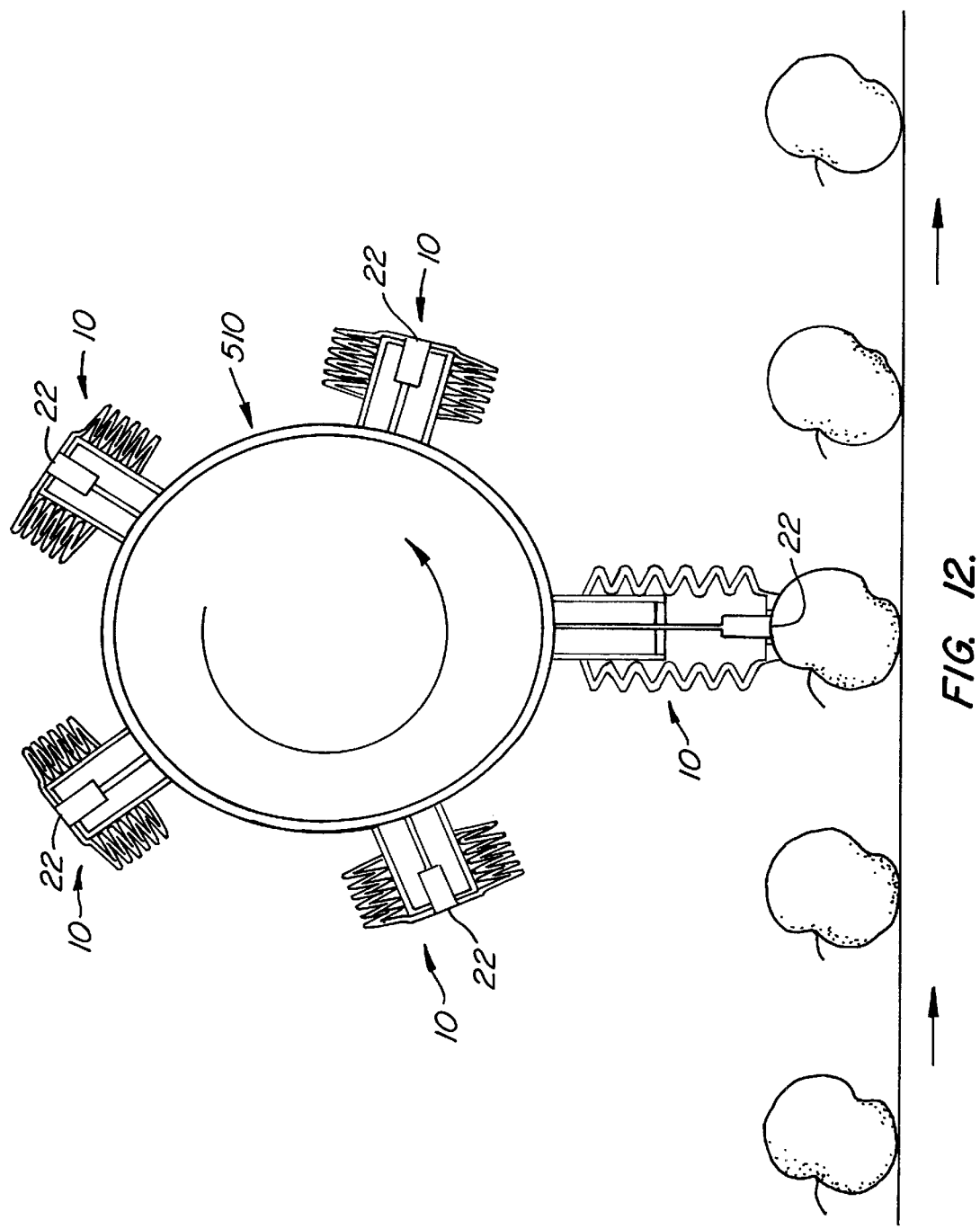
FIG. 12 shows a plurality of assemblies of the type shown in FIGS. 1 to 9 mounted on a rotatable mounting.

FIG. 12 shows an arrangement in which a plurality of bellows 10, each incorporating a sensor 22 of the type described in any of the embodiments mentioned above, are mounted on a rotatable mounting 510. The rotatable mounting 510 can be rotatably driven in such a manner that, as the fruit passes under the mounting on the conveyor, in turn each of the bellows 10 can be arranged to contact a fruit passing under the mounting. Preferably the sensors 22 in each bellows 10 will be of the same type; however, should it be required for any particular application, the sensors can be of different types.

In all embodiments, the output from the sensor is analyzed to form an output signal which is indicative of the maturity of the fruit or vegetable being measured. For example, in the embodiment of FIG. 1, a gas analyzer 31 is used. The present applicants have realized that it may be possible, especially when miniature sensors are used, for the means analysis to be incorporated within or closely associated with the sensor whereby the means for analysis is actually contained within the bellows 10 itself. This means that the output signal could be taken directly from the bellows 10 without necessitating further processing.

Further embodiments are shown in FIGS. 13 to 20.

Figure 13:
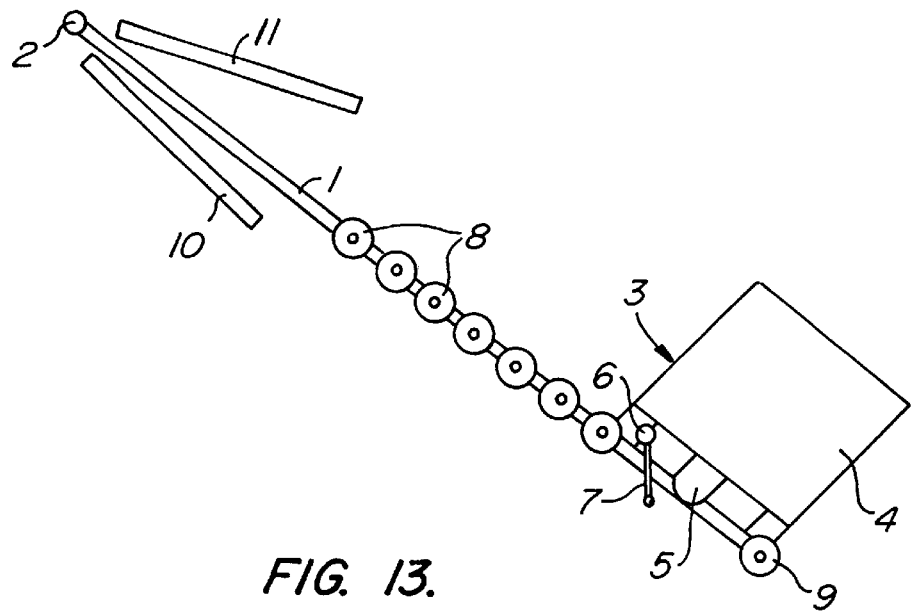
FIG. 13 is a schematic side view of one embodiment of the invention.

The apparatus illustrated in FIG. 13 is designed to tap test fruit, such as avocado pears, as they are conveyed along a so-called "singulator" which is used in sorting depots to place fruit into individual cups from which they are deposited into different hoppers depending on the degree of ripeness sensed by the test. The apparatus includes an impactor arm 1 which is pivoted at one end 2 above the singulator or conveyor (not shown) arranged to convey the items of fruit one at a time beneath the arm. At its outer end, the arm mounts the impactor device 3. The latter comprises a solenoid 4 having its armature 5 projecting at one end from the solenoid casing and serving as an impactor which is arranged to tap the fruit passing beneath the arm. The armature 5 is advanced to apply a tap to a fruit in response to an electrical driving pulse applied to the solenoid and is spring biased to return to its retracted position. The armature incorporates a force transducer in the form of a piezoelectric crystal which produces an electrical output pulse in response to the reaction force exerted on the armature as a result of applying a tap to a fruit. The solenoid 4 is triggered to apply a tap in response to the actuation of a microswitch 6 by a fruit travelling beneath the impactor and engaging a downwardly projecting actuating arm 7 of the microswitch.

Between the solenoid 4 and the pivot 2, the arm 1 is fitted with rollers 8 to permit the arm to ride smoothly over fruit travelling beneath and engaging the arm preparatory to being tapped by the impactor. The fruit is protected from damage by the outer end of the arm by a further roller 9. Suitable stops 10, 11 are mounted below and above the arm adjacent its pivot in order to limit movement of the arm and prevent it from dropping too low and engaging the conveyor or being raised too high.

Figure 14:
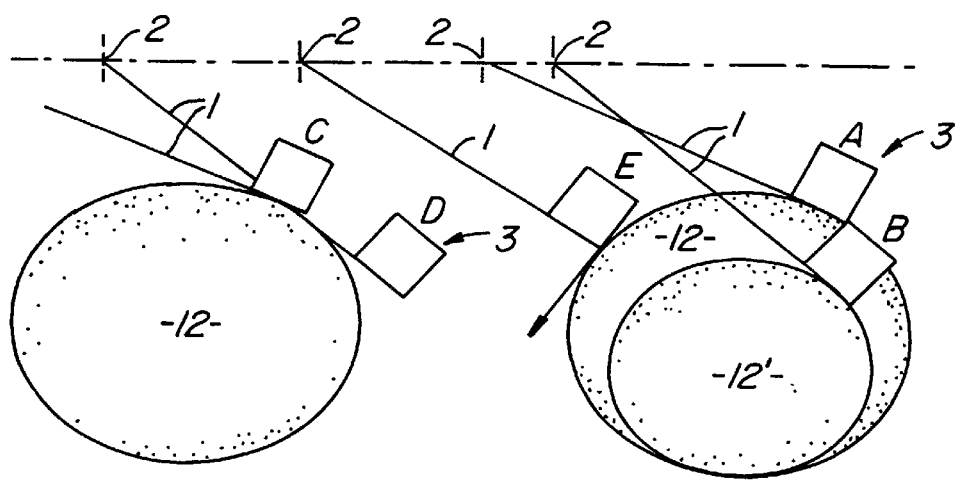
FIG. 14 is a schematic side view illustrating the motion sequence of the impactor device of FIG. 13 as it is engaged by fruit moving along a conveyor beneath the impactor device (for clarity the pivot position of the device is moved horizontally in this Figure whereas, in reality, the pivot of the device is fixed and the fruit travels past the device)

The conveyor is of a known construction and, desirably, it should position the avocado pears or other fruit under the impactor with the widest or most bulbous part of the fruit below the impactor. The fruit may be advanced along the conveyor with a rolling motion or be stationary about its axis. Referring also to FIG. 14, as each fruit 12 travels below the impactor arm 1, it engages the arm and pushes it upwards so as to move the impactor 3 into a position for tapping the fruit. When the fruit and impactor are in a predetermined position relative to one another, the fruit actuates the microswitch 6 by engaging the actuating arm 7 so that an electrical driving pulse is supplied to fire the solenoid 4 and the armature 5 is actuated to tap the fruit.

The firing position of the solenoid is at A on large fruit 12 and at B on small fruit 12' while the first contact position is C on large fruit and D on small fruit. These differences in contact positions are accommodated by firing the solenoid with the microswitch 6. After tapping, each fruit continues to travel beneath the arm 1 and subsequently the arm is released from the fruit (position E) and returns to a rest position against the lower stop preparatory to engaging the next fruit on the conveyor line. The roller 9 at the outer end of the arm protects the fruit from damage as the arm is released.

Figure 15:
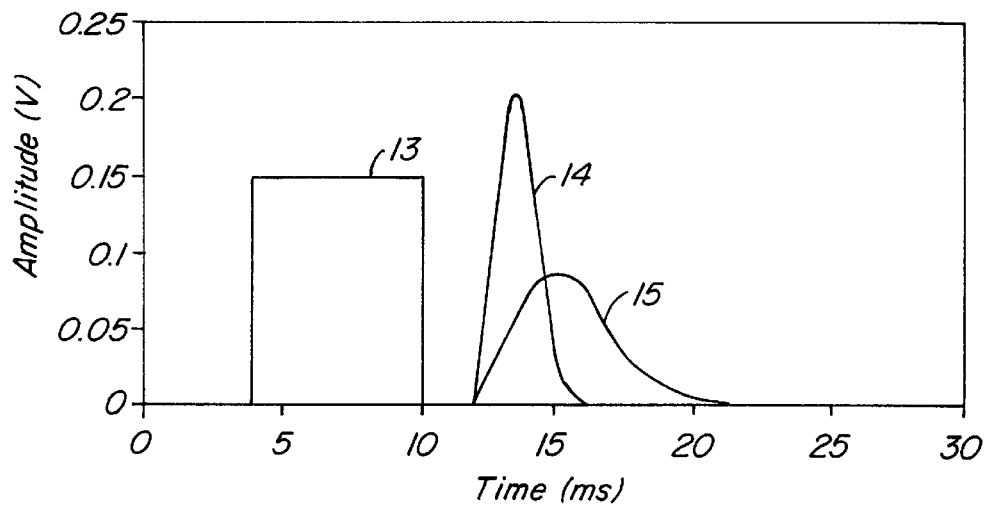
FIG. 15 is a voltage/time graph illustrating the shapes of the electrical driving pulse for the impactor and the output pulses resulting from tapping fruits of different firmness.

As shown in the graph of FIG. 15, the solenoid driving pulse 13 is a square pulse and has finished before the tap impacts on a fruit so that the solenoid 4 does not drive the armature into the fruit. The reaction force resulting from a tap applied by the solenoid armature striking the fruit is detected by the force transducer and is reproduced as a single electrical output pulse similar to pulses 14, 15 shown in FIG. 15. The peak value and duration of the resulting output pulse depends on the firmness and therefore the ripeness of the fruit. Hence, the pulse 14 represents the pulse resulting from a tap test on an unripe or hard avocado while pulse 15 results from a tap test on a ripe or soft avocado. These output pulses may be processed in any of the ways described above in order to produce a measurement indicative of the ripeness of the fruit.

Figure 16:
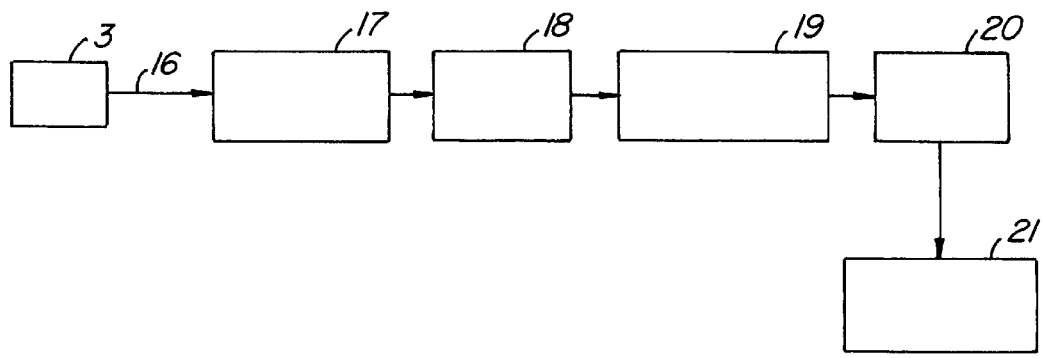
FIG. 16 is a block circuit diagram of signal processing circuitry suitable for use with the invention.

FIG. 16 illustrates an electronic circuit for use with the tapping device described above and for processing the electrical output pulses produced by the device upon tapping fruit. The output pulses from the piezoelectric transducer of the impactor device 3 are fed by way of leads 16, an amplifier 17 and trigger unit 18 to an analogue-to-digital converter 19 and then to a buffer store 20. The trigger unit 18 operates in response to actuation of the microswitch 6 and ensures that the value of the output from the amplifier 17 covers the full duration of the pulse. When required, the output from the store 20 is fed to a computer 21 which processes the digital signal from the store in any of the ways described above to produce a measurement indicative of the ripeness of the fruit. In order that the measurement can be provided as a numerical output directly indicative of the ripeness, it will be necessary to calibrate the measurements produced against known ripening data for each species of fruit and its individual cultivars.

Figure 17:
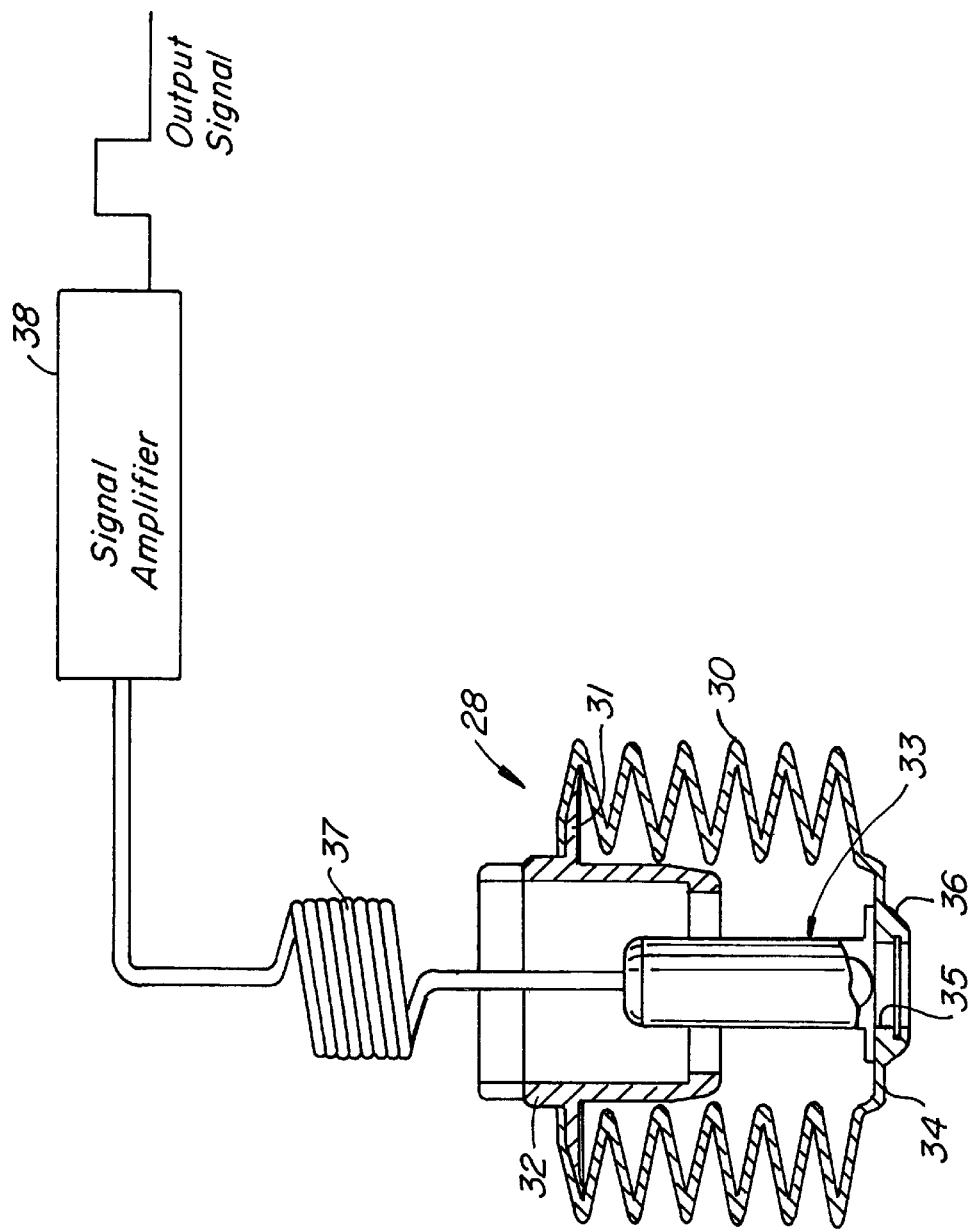
FIG. 17 is a diagrammatic partly sectional elevation of another embodiment of the invention.

Referring now to FIGS. 17 and 18, an alternative embodiment of the impactor device 28 comprises a bellows 30 of resilient material, such as plastics or synthetic rubber, and of lightweight construction. Such a bellows is already known in connection with labelling machines for example as described in U.S. Pat. No. 4,217,164. The bellows is mounted on the projecting annular flange 31 of a rigid, tubular support 32. Means (not shown) are provided for applying a vacuum to the bellows to hold it in a retracted disposition, as illustrated in FIG. 17, and when appropriate to supply pressurized air to the bellows to expand it downwardly (as viewed in FIG. 17).

An impactor 33 is mounted on the inner surface of the free end 34 of the bellows above an aperture 35 in a shaped nose piece 36 at the free end 34. The impactor 33 is movable with the bellows when the bellows is expanded and retracted. It is electrically coupled by wires 37 to an amplifier 38 for signals from the impactor.

The impactor 33 is shown in more detail in FIG. 18. It is mounted in a tubular housing 40 having an out-turned flange 41 at one end mounting the impactor on the inner surface of the free end 34 of the bellows 30. A cap 42 is provided at the opposite end of the housing which with said opposite end defines an internal annular shoulder or abutment 43.

The impactor, itself, comprises an inner housing 44 slidably disposed in housing 40. The end of the inner housing 44 adjacent the cap 42 is provided with a flange 45. A compression spring 46 is positioned around the inner housing and bears at one end on the shoulder 43 and at its opposite end on the flange 45 so that the inner housing is urged upwardly (as viewed in FIG. 18). The upward movement of the inner housing is limited by engagement of the inner housing against the cap 42.

Secured within the inner housing 44 is a solid slug 52 which mounts a piezoelectric transducer 50 adjacent the end 51 of the inner housing remote from the cap 42. The end 53 of the slug projects from the end 51 of the inner housing for striking a fruit to be tested and is part spherically shaped. The transducer 50 is mounted in contact with the slug and the signal wires 37 are fed to a cavity 54 providing access to opposite sides of the transducer and permitting connection of the wires 37 thereto, via an aperture 55 in the cap and passageways 56, 57 in the inner housing and slug (see also FIG. 19).

In operation fruit or vegetable items are conveyed in sequence by a conveyor past the bellows. When a fruit item is underneath the bellows, expansion of the bellows is effected in response to control means which can be similar to the control means used for labelling, as described in the aforementioned U.S. Pat. No. 4,217,164. The bellows expand until the nose piece 36 at the free end contacts the fruit or vegetable item. At that instant further expansion of the bellows stops. However, the impactor 33 which moves with the expanding bellows continues moving until the slug 52 impacts against the surface of the fruit or vegetable item. The reaction force exerted on the slug 52 causes the piezo-electric transducer 50 in contact with the slug to produce a signal which can then be processed in the same way as described in connection with FIG. 16.

Figure 20:
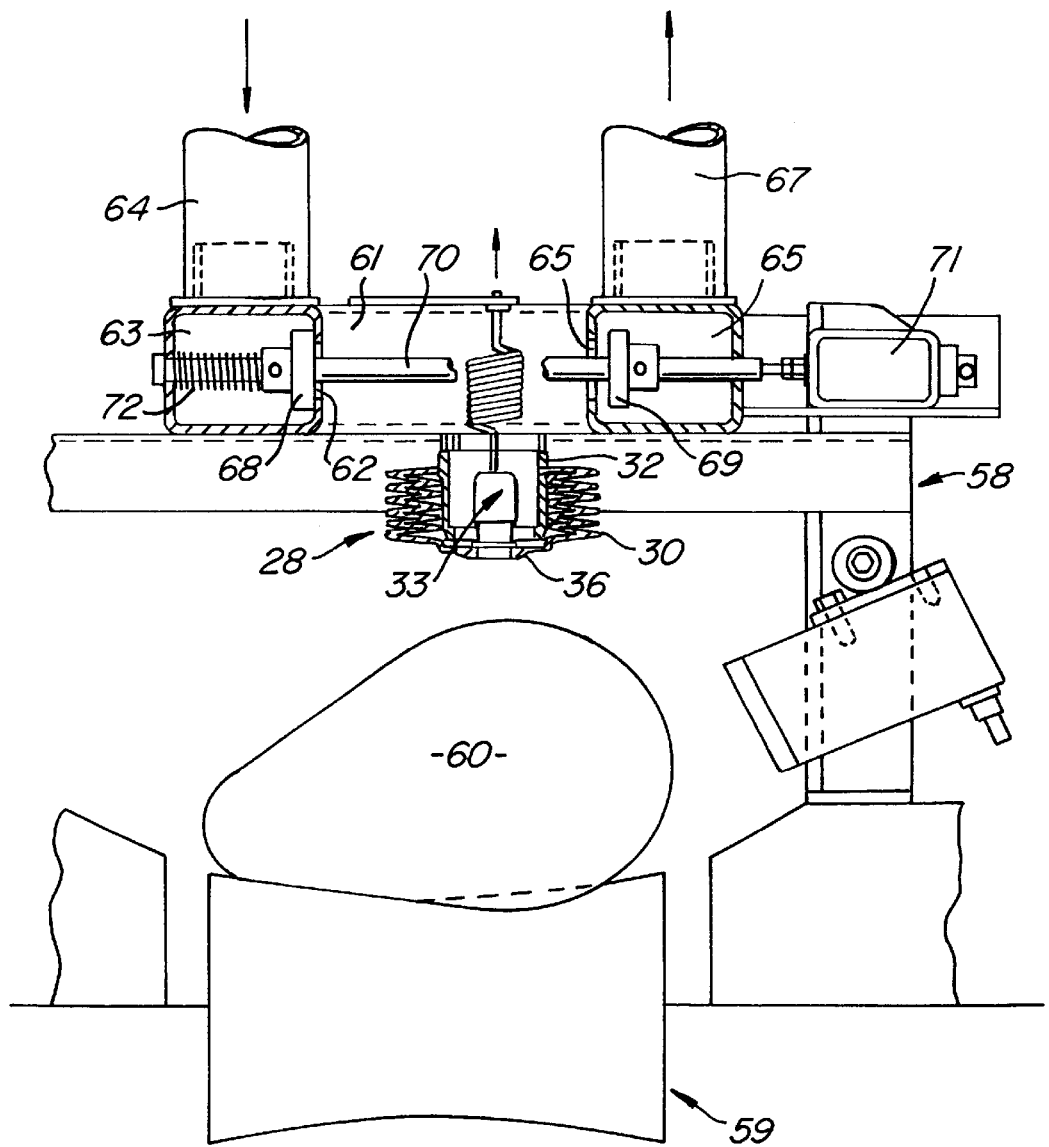
FIG. 20 is a view, partly in section, of apparatus embodying the impactor device of FIGS. 17 and 18 and taken transverse to the fruit conveyor.

In FIG. 20, the impactor device 28 is shown installed in a ripeness testing machine and mounted above a fruit 60 which is passing below the device. The latter is mounted on a frame structure 58 which is disposed above a conveyor 59 upon which the fruit 60 is transported.

The tubular support 32 for the bellows of the impactor device communicates with a chamber 61 mounted on the frame structure 58 above the device. The chamber 61 is connected at one side, via a port 62, to a pressurized air chamber 63 which is coupled to a source of air pressure by an inlet conduit 64. At its opposite side, the chamber 61 is connected, via a port 65, to a vacuum chamber 66 which is connected to a source of vacuum by a outlet conduit 67. The ports 62, 65 are controlled by valve members 68, 69 attached to a slidable valve rod 70 which is reciprocated by means of an electrical solenoid 71 and a return spring 72. The spring 72 urges the valve members 68, 69 into positions in which the air inlet port 62 is closed and the vacuum port 65 is open so that vacuum is applied to the support tube 32 and the bellows 30 are retained in a retracted rest position. Actuation of the solenoid 71 slides the valve control rod 70 against the action of the spring 72 to open the air inlet port 62 and close the vacuum port 65, thereby momentarily expanding the bellows so as to cause the nose 36 to contact a fruit 60 conveyed below the impactor device and the impactor to tap the fruit and produce an output pulse from the transducer 50. The solenoid 71 can be controlled in any convenient manner so as to actuate the impactor device as each fruit 60 is advanced below it. The solenoid is triggered so as to open the valve member 68 only briefly and apply air pressure to the bellows for a sufficient time to produce a driving force to initiate movement of the bellows and impactor towards the fruit, the arrangement being such that the impactor strikes the fruit under its own momentum when the nose piece 36 of the bellows contacts and stops against the fruit. Immediately thereafter, the bellows are contracted by exhaustion of air therefrom through the vacuum port 65 and vacuum outlet conduit 67 to return the impactor device to its rest position.

In order to optimize the ripeness measurement for each fruit, two or more impactor devices 28 may be mounted side-by-side in a row transversely of the conveyor 59 for simultaneously tapping each fruit so as to produce an output signal for each of a plurality of positions along the fruit axis disposed transversely to the direction of movement of the conveyor. The conveyor 59 may be adapted to rotate each fruit as it is advanced by the conveyor and a plurality of the impactor devices 28 may also be mounted in succession, or in successive rows, along the conveyor for successively tapping each fruit and producing an output signal for each of a plurality of positions about the fruit.

While particular embodiments have been described, it will be understood that modifications can be made without departing from the scope of the invention as defined by the appended claims. For example, the signal processing may not require that the analogue output signal from the piezo-electric transducer be converted into a digital signal for processing by the computer, in which event, the analogue-to-digital converter 19 may be omitted from the circuit. Moreover, the rollers 8, 9 on the impactor arm 1 may be replaced by strips of low friction material, such as PTFE.

I claim:

1. An assembly for measuring the condition of fruit and vegetables comprising plunger means and a passive sensor carried by the plunger means, said plunger means being adapted to bring the passive sensor into contact with, or adjacent to, an item of fruit or vegetable whereby the sensor reacts to a property of said fruit or vegetable item to produce a signal related to that property, wherein the plunger means comprises a resilient bellows which is capable of expansion under the action of pressurized air to bring the passive sensor into contact with, or adjacent to, an item of fruit or vegetable, and which is capable of contraction to move the sensor away from the item.

2. An assembly according to claim 1, wherein the sensor reacts to the production of surface gas by the fruit or vegetable item.

3. An assembly according to claim 1, wherein the sensor is operable to detect the chlorophyll fluorescence of the fruit or vegetable item.

4. An assembly according to claim 1, wherein the sensor is operable to detect the visible and Near Infra Red spectrograph of the fruit item or vegetable item.

5. An assembly according to claim 1, wherein the sensor is operable to detect the change in a capacitance of the fruit or vegetable item.

6. An assembly according to claim 3, wherein said sensor comprises an optical device.

7. An assembly according to claim 6 wherein the optical device comprises one or more optical fibers.

8. An assembly according to claim 5, wherein the sensor comprises a charged capacitor, the presence of a vegetable or fruit item adjacent to which causes a variation in the capacitance of the charged capacitor.

9. An assembly according to claim 1, wherein the plunger means comprises a resilient bellows assembly which is capable of expansion under the action of pressurized air and retraction by application of a vacuum, the expansion and retraction of the bellows being timed so as to coincide with the presentation of a fruit or vegetable item for assessment.

10. An assembly according to claim 1, wherein a plurality of plunger means are provided mounted rotatably on a mounting, each plunger means carrying a corresponding sensor, said mounting being capable of rotation so as to bring each plunger means in sequence into a position where it can bring a corresponding sensor into contact with, or move adjacent to, an item of fruit of vegetable to allow said sensor to react to a property of said fruit or vegetable.

11. An assembly according to claim 10, wherein each said plunger means comprises an expandable resilient bellows.

* * * * *